US 8,983,577 B2

(12) United States Patent
Hansis et al.

(10) Patent No.: US 8,983,577 B2
(45) Date of Patent: Mar. 17, 2015

(54) SYSTEM FOR DETERMINING THE ORIENTATION OF A CATHETER

(75) Inventors: Eberhard Sebastian Hansis, Menlo Park, CA (US); Michael Grass, Buchholz in der Northeide (DE)

(73) Assignee: Koninklijke Philips N.V., Eindhoven (NL)

( * ) Notice: Subject to any disclaimer, the term of this patent is extended or adjusted under 35 U.S.C. 154(b) by 133 days.

(21) Appl. No.: 13/148,092

(22) PCT Filed: Feb. 4, 2010

(86) PCT No.: PCT/IB2010/050515
§ 371 (c)(1),
(2), (4) Date: Aug. 5, 2011

(87) PCT Pub. No.: WO2010/092512
PCT Pub. Date: Aug. 19, 2010

(65) Prior Publication Data
US 2011/0295111 A1     Dec. 1, 2011

(30) Foreign Application Priority Data

Feb. 12, 2009 (EP) .................................... 09152652

(51) Int. Cl.
*A61B 5/00* (2006.01)
*A61B 19/00* (2006.01)
(Continued)

(52) U.S. Cl.
CPC ....... *A61B 19/54* (2013.01); *A61F 2002/30619* (2013.01); *A61M 25/0108* (2013.01); *A61F 2250/0097* (2013.01);
(Continued)

(58) Field of Classification Search
None
See application file for complete search history.

(56) References Cited

U.S. PATENT DOCUMENTS

| 5,054,492 | A | 10/1991 | Scribner et al. |
| 5,968,040 | A | 10/1999 | Swanson et al. |

(Continued)

FOREIGN PATENT DOCUMENTS

| WO | WO9846119 | 10/1998 |
| WO | WO0130254 | 5/2001 |

OTHER PUBLICATIONS

J. Palvolgyi, "On the Use of a Non-Isocentric C-Arm as a Brachytherapy Localiser and the Multiparametric Fit Method in Reconstruction of the Fletcher-Suit-Delclos Applicator", PhD Dissertation, Semmelseis University, Budapest, Hungary, 2001.

*Primary Examiner* — Long V Le
*Assistant Examiner* — Farshad Negarestan

(57) ABSTRACT

The present invention relates to a system for determining the orientation of a catheter (2). The system comprises a catheter (2), an asymmetric marker (11) attached to the catheter (2), and an imaging unit (25) for generating a projection image of the asymmetric marker (11), wherein the imaging unit (25) comprises a radiation source for generating radiation for projecting the asymmetric marker (11) in a projection plane and a detection unit for generating the projection image of the asymmetric marker (11) projected in the projection plane. The system comprises further an orientation determination unit for determining the orientation of the asymmetric marker (11) from the projection image of the asymmetric marker (11) and for determining the orientation of the catheter (2) from the determined orientation of the asymmetric marker (11). The asymmetric marker (11) is adapted such that the orientation of the asymmetric marker (11) is determinable from the projection image of the asymmetric marker (11) alone.

13 Claims, 5 Drawing Sheets

(51) Int. Cl.
  *G03B 42/02*    (2006.01)
  *A61F 2/30*     (2006.01)
  *A61M 25/01*    (2006.01)
(52) U.S. Cl.
  CPC .. *A61F 2250/0098* (2013.01); *A61B 2019/502* (2013.01); *A61B 2019/5238* (2013.01)
  USPC ............................ 600/424; 600/431; 600/433

(56) References Cited

U.S. PATENT DOCUMENTS

| | | | |
|---|---|---|---|
| 6,285,903 | B1 | 9/2001 | Rosenthal et al. |
| 6,493,575 | B1 | 12/2002 | Kesten et al. |
| 2005/0113686 | A1* | 5/2005 | Peckham ..................... 600/431 |
| 2006/0149166 | A1 | 7/2006 | Zvuloni |
| 2008/0146942 | A1 | 6/2008 | Dala-Krishna |

* cited by examiner

SYSTEM FOR DETERMINING THE ORIENTATION OF A CATHETER

FIELD OF THE INVENTION

The present invention relates to a system for determining the orientation of the catheter, an asymmetrical marker for attaching to a catheter for determining the orientation of the catheter, a catheter comprising the asymmetric marker, an orientation determination unit and methods and computer programs for determining the orientation of the catheter comprising the asymmetric marker.

BACKGROUND OF THE INVENTION

U.S. Pat. No. 6,493,575 B1 discloses a system for determining the orientation of a catheter. Radial marker bands surround the distal end of the catheter at predefined intervals. Furthermore, an asymmetric marker being wedge-shaped is attached proximal to the distal end of the catheter. For determining the orientation of the catheter a projection image of the radial marker bands, the asymmetric marker and the distal end of the catheter itself is needed.

SUMMARY OF THE INVENTION

This means the detection of a single marker on the projection image does not allow determining the orientation of the catheter, i.e. at least the radial marker bands, the distal end of the catheter and the asymmetrical marker have to be imaged. These different elements have to be recognized in the projection image by a recognition unit, wherein for each of these different elements another recognition algorithm has to be used. In addition, the shape and orientation of the different recognized elements have to be combined for determining the orientation of the catheter. This determination of the orientation of the catheter is very complex and time consuming.

It is an object of the present invention to provide a system for determining the orientation of a catheter, an asymmetric marker for attaching to a catheter for determining the orientation of the catheter, a catheter comprising the asymmetric marker, an orientation determination unit and methods and computer programs for determining the orientation of the catheter comprising the asymmetric marker, which allow a less complex and less time consuming determination of the orientation of the catheter.

In an aspect of the present invention a system for determining the orientation of a catheter is provided, wherein the system comprises:

a catheter, an asymmetric marker attached to the catheter, an imaging unit for generating a projection image of the asymmetric marker, wherein the imaging unit comprises a radiation source for generating radiation for projecting the asymmetric marker in a projection plane and a detection unit for generating the projection image of the asymmetric marker projected in the projection plane, an orientation determination unit for determining the orientation of the asymmetric marker from the projection image of the asymmetric marker and for determining the orientation of the catheter from the determined orientation of the asymmetric marker, wherein the asymmetric marker is adapted such that the orientation of the asymmetric marker is determinable from the projection image of the asymmetric marker alone.

Since the asymmetric marker is adapted such that the orientation of the asymmetric marker is determinable from the projection image of the asymmetric marker alone, it is not required to recognize different elements in the projection image, in particular, it is not necessary to recognize radial marker bands, a wedge-shaped asymmetric marker and the distal end of the catheter itself. One or several asymmetric markers can be attached to the catheter, wherein only this or these asymmetric markers have to be recognized in the projection image, i.e. it is not necessary to provide different recognition algorithms for different kinds of elements. This reduces the complexity and the time needed for determining the orientation of the catheter.

Since the asymmetric marker is adapted such that the orientation of the asymmetric marker is determinable from the projection image of the asymmetric marker alone, for each asymmetric marker attached to the catheter the orientation of the respective asymmetric marker at the location at which the respective asymmetric marker is attached to the catheter can be determined, if several of the asymmetric markers are attached to the catheter. Since the position and orientation of the asymmetric markers with respect to the catheter are known, the orientation determination unit can determine the orientation of the catheter based on the determined orientations of the asymmetric markers.

The catheter is preferentially a catheter that is adapted for being used during electrophysiological interventions, in particular, electrophysiological ablation interventions. For example, the catheter is an ablation catheter allowing ablating an object, in particular, heart tissue of a heart wall, if the catheter is located within a heart. In addition or alternatively, the catheter can comprise elements for sensing and/or irrigating an object in which the catheter is locatable. For example, the catheter can be adapted to be locatable in a heart of a human being or an animal or within another object like another organ or a technical object.

The imaging unit is a projection unit allowing generating projection images of the asymmetric marker. Preferentially, the imaging unit is an X-ray fluoroscopy device for providing two-dimensional projection images of the asymmetric marker, in particular, while the catheter is located within an object like a heart of a human being or an animal. Preferentially, the imaging unit is adapted for providing projection images during an electrophysiological intervention. This allows determining the orientation of the catheter during such an electrophysiological intervention.

The asymmetric marker is adapted such that the orientation of the asymmetric marker is determinable from the projection image of the asymmetric marker alone. This means preferentially that at least the degree of angulation and the direction of angulation with respect to the projection plane are determinable by the asymmetric marker alone.

It is further preferred that the asymmetric marker is asymmetric under mirroring with respect to all spatial axes.

It is further preferred that the asymmetric marker comprises a ring element and at least one asymmetric element attached to the ring element. The ring element preferentially surrounds the catheter. Preferentially, two asymmetric elements are attached to the ring element.

It is further preferred that the at least one asymmetric element is v-shaped, wherein the two legs of the at least one v-shaped asymmetric element are distinguishable in the projection image. Preferentially, one of the legs of the at least one v-shaped asymmetric element is shorter than the other of the legs of the at least one v-shaped asymmetric element for distinguishing the two legs in the projection image.

It is further preferred that the at least one asymmetric element is v-shaped, wherein an end element is located at an end of a leg of the at least one v-shaped asymmetric element for distinguishing the two legs. The end element has preferentially a dimension in a direction being traverse, in particular, orthogonal, to the longitudinal direction of the leg, at which end the end element is located, being larger than the diameter of this leg. The end element is preferentially a spherical element having a diameter larger than the diameter of the leg at which the end element is located. It is further preferred that the end element is located at the end of a longer leg of the v-shaped asymmetric element.

It is further preferred that the orientation determination unit is adapted to determine the degree of angulation with respect to the projection plane from the eccentricity of the ring element in the projection image and to determine the direction of angulation with respect to the projection plane from the arrangement of the at least one asymmetric element in the projection image.

For example, for a part of the catheter, at which the asymmetric marker is located, running parallel to the projection plane or the detection unit the ring element may be seen as a line only, whereas for this part of the catheter running orthogonal to the projection plane or the detection unit, the ring may be seen as a circle. For all other angulations the ring element may appear as an ellipse, whose eccentricity determines the catheter angle with respect to the projection plane or the detection unit. A remaining ambiguity whether the respective part of the catheter is inclined towards the projection plane or the detection unit or away from it, is resolved by analyzing the at least one asymmetric element, in particular, by analyzing the location of the two legs of the v-shaped at least one asymmetric element. The system can be calibrated by detecting the appearance of the at least one asymmetric element in the projection image, if the catheter is in a known inclination position. Thus, by calibration an appearance of the at least one asymmetric element can be assigned to an inclination towards or away from the projection plane, wherein this assignment can be used by the orientation determination unit for determining the inclination of the catheter.

It is preferred that two asymmetric elements are v-shaped, two legs of each v-shaped asymmetric element are distinguishable in the projection image, for both asymmetric elements a connection point of the two legs is attached to the ring element, the two asymmetric elements are arranged at opposite sides of the ring element with respect to a plane in which the ring element is located, if in a clockwise direction a first leg of one of the asymmetric elements is located in front of a second leg, in the counter-clockwise direction the first leg of the other of the asymmetric elements is located in front of the second leg, the orientation determination unit is adapted to determine that the catheter is tilted, away from the projection plane, if a) the asymmetric elements appear inside the ring element and for both asymmetric elements the first leg appears left of the second leg or b) the asymmetric elements appear outside of the ring element and for both asymmetric elements the first leg appears right of the second leg, towards the projection plane, if c) the asymmetric elements appear inside the ring element and for both asymmetric elements the first leg appears right of the second leg of the asymmetric element or d) the asymmetric elements appear outside of the ring element and for both asymmetric elements the first leg of the asymmetric elements appears left of the second leg.

It is further preferred that the system comprises a multitude of asymmetric markers, wherein the asymmetric markers are attached in predefined intervals along the catheter.

It is further preferred that the multitude of asymmetric markers is attached to segments of the catheter, wherein the orientation determination unit is adapted to determine the orientation of the multitude of asymmetric markers from the projection image and to determine the orientations of the segments of the catheter from the determined orientation of the multitude of asymmetric markers, wherein the orientation determination unit further comprises a catheter model providing unit for providing a model of the catheter and a catheter path determination unit for determining a path of the catheter by arranging the provided model of the catheter such that it corresponds to the determined orientations of the segments of the catheter. The catheter model is, for example, an elasto-mechanical model of the catheter, wherein it is assumed that the catheter can only be bent smoothly, i.e. without kinking.

If several asymmetric markers are present, for several asymmetric markers the orientation can be determined, thereby allowing determining the orientation of the catheter path, in particular, in three-dimensions, possibly with the aid of the catheter model.

It is further preferred that the catheter path determination unit is adapted to determine the path of the catheter based on the path of the catheter in the projection image.

It is further preferred that the imaging unit is adapted to project the multitude of asymmetric markers in the projection plane and to generate a projection image of the multitude of asymmetric markers projected in the projection plane, wherein the catheter path determination unit is adapted to determine the path of the catheter projected in the projection plane from the projection image of the multitude of asymmetric elements.

It is further preferred that a linear marking element is arranged along the length of the catheter. The linear marking element is preferentially arranged along the center of the catheter. The linear marking element is preferentially a wire.

It is further preferred that the imaging unit is adapted to project the linear marking element in the projection plane and to generate a projection image of the linear marking element projected in the projection plane, wherein the catheter path determination unit is adapted to determine a path of the catheter projected in the projection plane from the projection image of the linear marking element.

It is further preferred that the catheter path determination unit is adapted to determine the position of the path of the catheter along the path of the radiation generating the projection image based on predefined constraints defining possible positions of the path of the catheter along the path of the radiation. In particular, it is preferred that the catheter path determination unit is adapted to determine an absolute shift of the whole catheter in a direction perpendicular to the projection plane based on predetermined constraints of the catheter path. For example, anatomical constraints can be present if the catheter is arranged within an organ like the heart. If, for example, the catheter is arranged within a known object, wherein the location and the orientation of the object is known, for example, within a heart with known anatomy, possible positions of the whole catheter, in particular, in a direction perpendicular to the projection plane, are known and can be used to determine the absolute shift of the whole catheter in this direction.

It is further preferred that at least two of the asymmetric markers are rotated with respect to each other and with respect to a rotation axis located along the length and along the center of the catheter. This ensures that some asymmetric elements are always visible with little foreshortening regardless of the rotation of the catheter around its axis.

In a further aspect of the present invention an asymmetric marker for attaching to a catheter for determining the orientation of the catheter from a determined orientation of the asymmetric marker is provided, wherein the asymmetric marker is adapted to allow determining the orientation of the asymmetric marker from a projection image of the asymmetric marker alone generated by an imaging unit comprising a radiation source for generating radiation for projecting the asymmetric marker in a projection plane and a detection unit for generating the projection image of the asymmetric marker projected in the projection plane.

In a further aspect of the present invention, a catheter comprising an asymmetric marker as defined in claim 9 is provided.

In a further aspect of the present invention an orientation determination unit is provided, wherein the orientation determination unit is adapted to determine the orientation of an asymmetric marker from a projection image of the asymmetric marker and to determine the orientation of a catheter from the determined orientation of the asymmetric marker, the asymmetric marker being attached to the catheter, the projection image being generated by an imaging unit, wherein the imaging unit comprises a radiation source for generating radiation for projecting the asymmetric marker in a projection plane and a detection unit for generating the projection image of the asymmetric marker projected in the projection plane, wherein the asymmetric marker is adapted such that the orientation of the asymmetric marker is determinable from the projection image of the asymmetric marker alone.

In a further aspect of the present invention a method for determining the orientation of a catheter comprising an asymmetric marker is provided, the method comprising following steps:

generating a projection image of the asymmetric marker by an imaging unit, wherein the imaging unit comprises a radiation source for generating radiation for projecting the asymmetric marker in a projection plane and a detection unit for generating the projection image of the asymmetric marker projected in the projection plane, determining the orientation of the asymmetric marker from the projection image of the asymmetric marker alone, determining the orientation of the catheter from the determined orientation of the asymmetric marker.

In a further aspect of the present invention an orientation determination method is provided, the method comprising following steps:

determining the orientation of an asymmetric marker from a projection image of the asymmetric marker, determining the orientation of a catheter from the determined orientation of the asymmetric marker, the asymmetric marker being attached to the catheter, the projection image being generated by an imaging unit, wherein the imaging unit comprises a radiation source for generating radiation for projecting the asymmetric marker in a projection plane and a detection unit for generating the projection image of the asymmetric marker projected in the projection plane, wherein the asymmetric marker is adapted such that the orientation of the asymmetric marker is determinable from the projection image of the asymmetric marker alone.

In a further aspect of the present invention a computer program for determining the orientation of a catheter comprising an asymmetric marker is provided, the computer program comprising program code means for causing a system as defined in claim 1 to carry out the steps of the method, when the computer program is run on a computer controlling the system.

In a further aspect of the present invention a computer program for determining the orientation of a catheter comprising an asymmetric marker is provided, the computer program comprising program code means for causing a orientation unit to carry out the steps of the orientation method, when the computer program is run on a computer controlling the orientation unit.

It shall be understood that the system of claim 1, the asymmetric marker of claim 9, the catheter, the orientation determination unit, the method and the computer programs have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
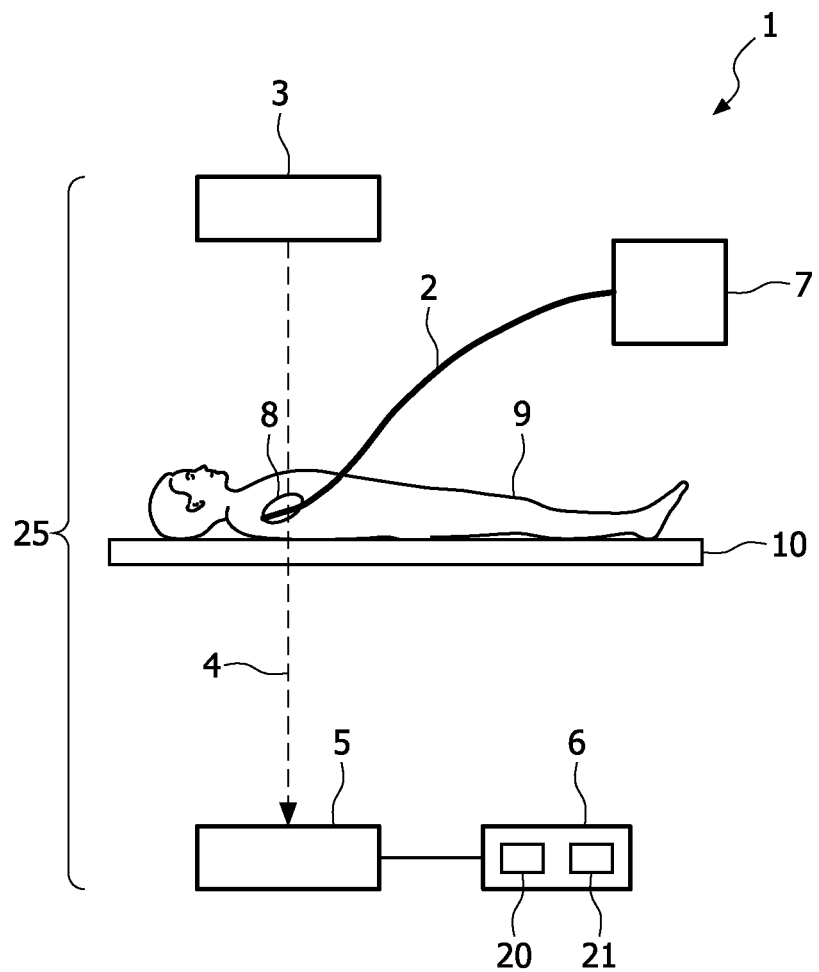
FIG. 1 shows schematically and exemplarily a system for determining the orientation of a catheter.

FIG. 1 shows schematically and exemplarily a system 1 for determining the orientation of a catheter 2. This system 1 comprises a catheter 2 and an asymmetric marker attached to the catheter. The asymmetric marker will be explained further below with reference to, for example, FIGS. 2 and 3. The system 1 for determining the orientation of the catheter 2 further comprises an imaging unit 25 for generating a projection image of the asymmetric marker, wherein the imaging unit 25 comprises a radiation source 3 for generating radiation 4 for projecting the asymmetric marker in a projection plane and a detection unit 5 for generating the projection image of the asymmetric marker projected in the projection plane.

The detection unit 5 comprises preferentially a two-dimensional detection surface, wherein the projection plane is located on the two-dimensional detection surface.

The imaging unit 25 comprising the radiation source 3 and the detection unit 5 is, in this embodiment, an X-ray fluoroscopy imaging unit for generating two-dimensional X-ray projection images.

The system 1 further comprises an orientation determination unit 6 for determining the orientation of the asymmetric marker from the projection image of the asymmetric marker and for determining the orientation of the catheter 2 from the determined orientation of the asymmetric marker.

The catheter 2 is controlled by a catheter control unit 7. The catheter 2 is preferentially an ablation catheter for ablating heart tissue of a heart wall. In FIG. 1, the distal end of the catheter 2 has been introduced into a heart 8 of a person 9 for performing an electrophysiological ablation intervention. The person 9 is located on a patient table 10.

The catheter control unit 7 and the catheter 2 are adapted to steer the catheter 2 into and within the heart 8 of the person 9. Furthermore, the ablation control unit 7 and the catheter 2 are adapted to apply ablation energy to the heart tissue. For example, the catheter comprises ablation elements for applying electrical energy like radio frequency energy to the heart tissue. Alternatively or in addition, the catheter 2 and the catheter control unit 7 can be adapted to use light energy, for example, of a laser source and/or microwaves for ablation and/or to perform a cryo-ablation procedure. The catheter control unit 7 and catheter 2 can further be adapted to sense the heart tissue, for example, by using sensing elements like sensing electrodes for measuring electrical signals of the heart. The catheter control unit 7 and the catheter 2 can further be adapted to irrigate and/or cool heart tissue, in particular, ablated heart tissue.

Figure 2:
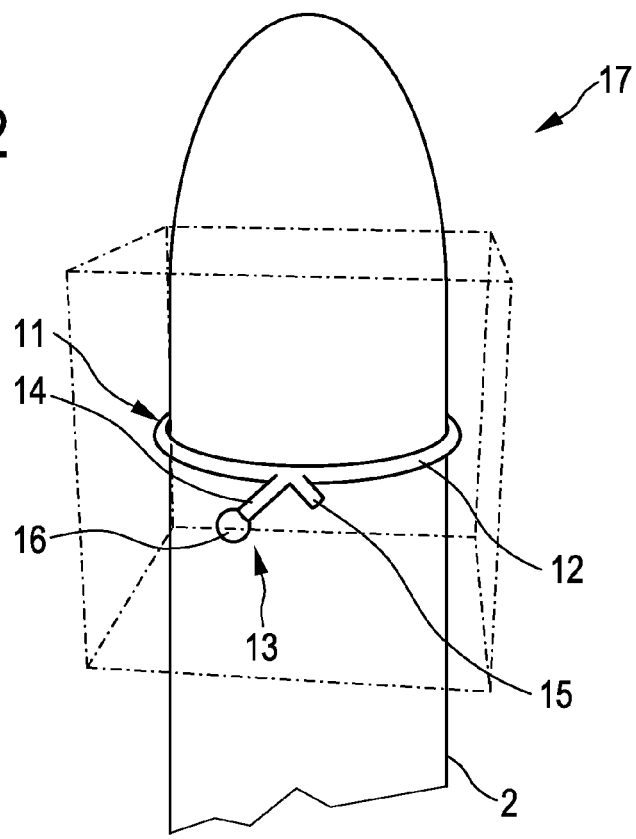
FIG. 2 shows schematically and exemplarily a distal end of a catheter to which an asymmetric marker is attached.
Figure 3:
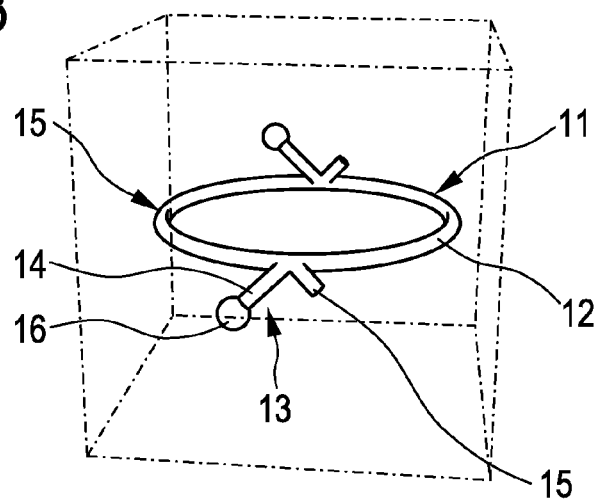
FIG. 3 shows schematically and exemplarily an asymmetric marker.

FIG. 2 shows schematically and exemplarily a distal end 17 of the catheter 2. The asymmetric marker 11 has been attached to the distal end 17 of the catheter 2. The asymmetric marker 11 without the catheter is schematically and exemplarily shown in FIG. 3.

The asymmetric marker 11 comprises a ring element 12 and at least one asymmetric element 13. In this embodiment, two asymmetric elements 13 are attached to the ring element 12. The ring element 12 surrounds the distal end 17 of the catheter 12.

The asymmetric elements 13 are v-shaped, wherein one of the legs of the v-shaped asymmetric element 13 is longer than the other leg of the v-shaped asymmetric element, i.e. the asymmetric element 13 has a longer leg 14 and a shorter leg 15. An end element 16 is located at the end of the longer leg 13 pointing away from a connection of the two legs 14, 15. In another embodiment, the end element 16 can be missing or the two legs 14, 15 can have the same length.

The end element 16 has a dimension in a direction being traverse, in particular, orthogonal, to the longitudinal direction of the leg 14 being larger than the diameter of the leg 14. The end element 16 is preferentially a spherical element having a diameter larger than the diameter of the leg 14.

The connection point of the two legs 14, 15 of the asymmetrical element 13 is attached to the ring element 12 such that the two legs 14, 15 and the end element 16 do not protrude into an imaginary cylinder having an outer diameter similar to the inner diameter of the ring element 12 and surrounded by the ring element 12.

Preferentially, the asymmetric marker 11 comprises two asymmetric elements 13, wherein the two asymmetric elements 13 are arranged at opposite sides of the ring element 12 with respect to a plane in which the ring element 12 is located. It is further preferred that, if in a clockwise direction the longer leg and/or the leg with the end element of one of the asymmetric elements is located in front of the other leg, in the counter-clockwise direction the longer leg and/or the leg with the end element of the other of the asymmetric elements is located in front of the other leg.

The asymmetric marker 11 is asymmetric under mirroring with respect to all spatial axes. In another embodiment, instead of the asymmetric element 11 any other asymmetric element being asymmetric under mirroring with respect to all spatial axes, can be used. Examples for other asymmetric elements are described further below with reference to FIGS. 7 to 9.

Figure 4:
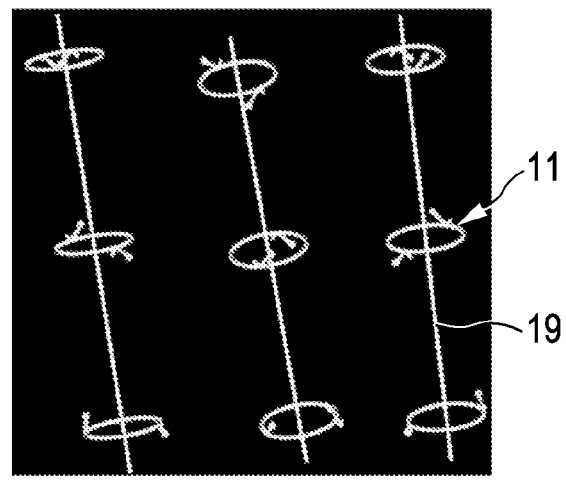
FIG. 4 shows schematically and exemplarily asymmetric markers and linear elements of three catheters.

The catheter can comprise several asymmetric markers. Furthermore, several catheters can be used during an electrophysiological intervention within the heart 8 of the person 9. Several catheters with several asymmetric markers 11 and a linear marking element 19 are schematically and exemplarily shown in FIG. 4.

The linear marking element 19 is preferentially arranged along the centre of the respective catheter and is preferentially a wire.

The orientation determination unit 6 is adapted to determine the orientation of the respective asymmetric marker 11 from the projection image of the asymmetric marker. The orientation determination unit 6 is adapted to determine a degree of angulation of the part of the catheter at which the respective asymmetric marker is located as an angle between the projection plane, i.e. e.g. the plane in which the two-dimensional detection surface is located, and the part of the catheter at which the respective asymmetric marker is located form the eccentricity of the ring element 12 in the projection image. Since the geometry of the radiation for traversing the heart 8 and the geometry of the ring element 12 are known, this degree of angulation can be determined based on the eccentricity of the ring element 12 in the projection image. For example, if the part of the catheter, at which the respective asymmetric marker is located, is parallel to the two-dimensional detection surface, the ring element 12 may be seen as a line only, whereas, if the part of the catheter at which the asymmetric marker is located runs orthogonal to the two-dimensional detection surface, the ring element 12 may be seen as a circle. For all other angulations the ring element may appear as an ellipse, whose eccentricity determines the angle between the part of the catheter at which the asymmetric marker is located and the two-dimensional detection surface. The imaging unit and the orientation determination unit can be calibrated by determining the eccentricity of a ring element 12 in a projection image for different known angular positions of the asymmetric marker. This allows determining the degree of angulation, i.e. the angle of the part of the catheter at which the asymmetric marker is located with respect to the two-dimensional detection surface, by analyzing the eccentricity of the ring element 12 of the asymmetric marker 11. A remaining ambiguity, whether the respective part of the catheter is inclined towards the two-dimensional detection surface or away from the two-dimensional detection surface, is resolved by analyzing the asymmetric elements 13. The imaging unit and the orientation determination unit can be calibrated by inclining a part of a catheter comprising an asymmetric marker towards and away from the two-dimensional detection surface and by assigning the orientation of the asymmetric elements in the projection image to the respective inclinations of the part of the catheter at which the asymmetric marker is located. This allows determining whether the part of the catheter at which the respective asymmetric marker is located is tilted forward or backward with respect to the two-dimensional detection surface by analyzing the orientation of the asymmetrical elements in the projection image.

In an embodiment, the orientation determination unit is adapted to determine whether the asymmetric elements 13 appear inside or outside of the ring element 12 and whether the longer leg 14 and/or the leg 14 comprising the end element 16 appears left or right of the shorter leg 15. The orientation determination unit is preferentially further adapted to determine that the part of the catheter at which the respective asymmetrical marker is located is tilted away from the two-dimensional detection surface, if a) the asymmetric elements appear inside the ring element and the longer leg and/or the leg comprising the end element appears left of the shorter leg or b) the asymmetric elements appear outside of the ring element and the longer leg and/or the leg comprising the end element appears right of the longer leg. It is further preferred that the orientation determination unit is adapted to determine that the part of the catheter at which the respective asymmetric marker is located is tilted towards the two-dimensional detection surface, if c) the asymmetric elements appear inside the ring element and if the longer leg and/or the leg comprising the end element appears right of the shorter leg of the asymmetric element or d) the asymmetric elements appear outside of the ring element and the longer leg and/or the leg comprising the end element of the asymmetric elements appears left of the shorter leg.

The several asymmetric markers 11 attached to a catheter are rotated with respect to each other if the parts of the catheter at which these asymmetric markers are located are not rotated with respect to each other. This means that, if the parts of the catheter at which the asymmetric markers are located are not rotated with respect to each other, the asymmetric elements 13 of at least two neighbored asymmetric markers do not coincide in a direction parallel to the catheter. The orientation determination unit can be calibrated by detecting an asymmetric marker in the projection image, if the rotational position of this marker around a rotational axis defined by the longitudinal catheter direction and/or an axis arranged centrally within the ring element, is known. Thus, different appearances of the asymmetric marker in the projection image are assigned to different rotational positions by calibration, wherein these assignments can be used by the orientation determination unit for determining the rotational position of the asymmetric marker. If the rotational positions of several asymmetric markers attached to several segments of the catheters are determined, twisting of the catheter can be determined.

The multitude of asymmetric markers 11 is attached to segments of the catheter 2, wherein the orientation determination unit 6 is adapted to determine the orientation of the multitude of asymmetric markers 11 from the projection image and to determine the orientations of the segments of the catheter 2 from the determined orientation of the multitude of asymmetric markers 11. The orientation determination unit 6 comprises a catheter model providing unit 20 for providing a model of the catheter 2 and a catheter path determination unit 21 for determining a path of the catheter 2 by arranging the provided model of the catheter such that it corresponds to the determined orientations of the segments of the catheter 2. The catheter model is, for example, an elasto-mechanical model of the catheter, wherein it is assumed that the catheter can be bended smoothly, i.e. without kinking.

It is further preferred that the catheter path determination unit 21 is adapted to determine the path of the catheter based on the determined orientations of the asymmetric elements and on the path of the catheter in the projection image. The path of the catheter in the projection image is preferentially determined from the projection image of the multitude of asymmetric elements. The catheter path determination unit 21 can also be adapted to determine a path of the catheter projected in the projection plane from the projection image of the linear marking element 19, if present.

The catheter path determination unit 21 is further adapted to determine the position of the path of the catheter along the path of the radiation generating the projection image based on predefined constraints defining possible positions of the path of the catheter along the path of the radiation. In particular, it is preferred that the catheter path determination unit 21 is adapted to determine an absolute shift of the whole catheter in a direction perpendicular to the projection plane based on predetermined constraints of the catheter path. For example, anatomical constraints can be present if the catheter 2 is arranged within an organ like the heart 8. If, for example, the catheter 2 is arranged within a known object, wherein the location and the orientation of the object is known, for example, within a heart with known anatomy, possible positions of the whole catheter, in particular, in a direction perpendicular to the projection plane, are known and can be used to determine the absolute shift of the whole catheter in this direction.

In an embodiment, the determined catheter path in the projection plane can be used to determine, at each marker position, the direction component parallel to the projection plane into which the catheter points at the respective marker position. As described above, the appearance of the marker assembly in the projection image can be used to determine the direction of the catheter to the projection plane, i.e. the component of the catheter direction perpendicular to the projection plane. Taken together, this defines the direction into which the catheter points at the respective marker position in three dimensions. In particular, if several markers are attached to the catheter, and if the catheter direction is determined for each of the markers, an elasto-mechanical model can be used to determine the three-dimensional path of the catheter. Since the catheter can only be bent smoothly and since its direction is known at several points along its path, its complete path can be reconstructed from the known directions, by fitting the elasto-mechanical model to the known catheter directions. In fitting the model, it can be exploited that the catheter path parallel to the projection plane is known from the projection image. A component of the path perpendicular to the projection plane can be determined by using the constraint defining possible positions of the path of the catheter along the path of the radiation.

Figure 5:
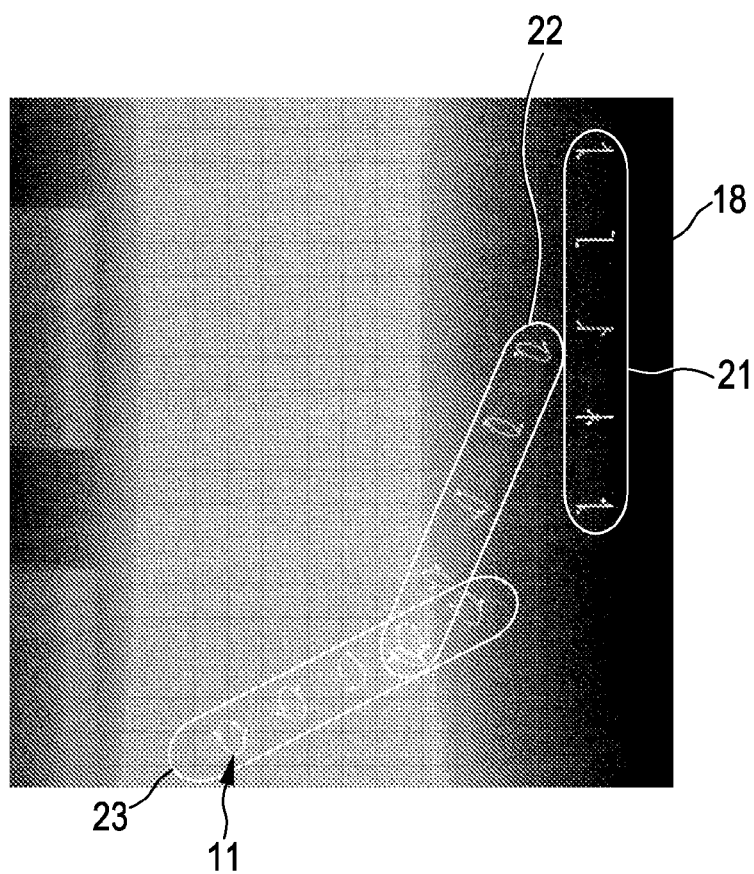
FIG. 5 shows schematically and exemplarily a projection image showing asymmetric markers of three catheters.

FIG. 5 shows schematically and exemplarily a projection image 18 of three catheters with different angulations inside a thorax of a person. The catheter comprising the asymmetric markers within the ellipse 21 runs substantially parallel to the two-dimensional detection surface, i.e. the ring elements appear substantially as lines. The catheter comprising the asymmetric markers within the ellipse 23 runs substantially orthogonal to the detection surface, i.e. the ring elements appear substantially as almost circular. The catheter comprising the asymmetric markers within the ellipse 22 comprises a degree of angulation between the degrees of angulation of the catheters comprising the asymmetric markers in the ellipse 21 and 23, respectively, i.e. the asymmetric markers within the ellipse 22 appear to be clearly elliptical having an eccentricity larger than the eccentricity of the asymmetric markers within the ellipse 23.

In FIG. 5, it is assumed that substantially only the asymmetric markers 11 can be seen in the projection image 18. However, generally in the projection image also other parts of the catheter and parts of the object, for example, of the heart of a person are shown.

Since the asymmetric markers are attached to the catheter, by determining the orientation of the asymmetric markers the orientation of the parts of the catheter at which the asymmetric markers are located is determined. By connecting these determined orientations of the parts of the catheter, for example, by using an elastic model of the catheter, the orientation of the catheter can be determined and shown, for example, on a display.

Figure 6:
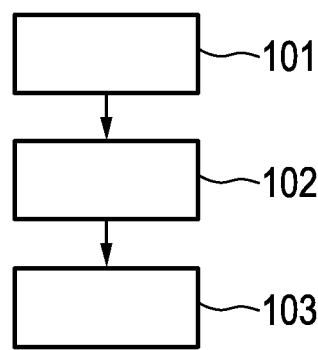
FIG. 6 shows exemplarily a flowchart illustrating a method for determining the orientation of a catheter and FIGS. 7 to 9 show schematically further exemplarily embodiments of asymmetric markers.

In the following a method for determining the orientation of a catheter comprising an asymmetric marker will be exemplarily described with respect to a flowchart shown in FIG. 6.

The catheter 2 has been introduced into the heart 8 of the patient 9, and in step 101 the imaging unit 25 generates a projection image of the asymmetric marker or of the multitude of asymmetric markers, wherein the radiation source 3 generates radiation 4 for projecting the asymmetric marker 11 or the multitude of the asymmetric markers in a projection plane and wherein a projection image of the asymmetric marker 11 or the multitude of asymmetric markers projected in the projection plane is generated by the detection unit by detecting the radiation.

In step 102, the orientation of the asymmetric marker 11 or of the multitude of asymmetric markers 11 is determined from the projection image of the asymmetric marker or of the multitude of asymmetric markers alone. In step 103, the orientation of the catheter is determined from the determined orientation of the asymmetric marker 11 or of the multitude of asymmetric markers 11, in particular, the path of the catheter is determined, in particular, in three dimensions, wherein preferentially a model of the catheter is arranged such that it corresponds to the determined orientations of the asymmetric markers attached to the catheter. Furthermore, preferentially the path of the catheter in the projection image and/or known constraints defining possible positions of the path of the catheter along the path of the radiation are used additionally for determining the catheter path in three dimensions.

The determination of the orientation of the catheter is preferentially performed during an electrophysiological ablation intervention, thereby allowing monitoring the catheter while performing the ablation procedure.

The asymmetric marker is of course visible in the projection image, i.e. the asymmetric marker is preferentially a radio-opaque marker which is preferentially made of a metal like gold. Also other radio-opaque materials can be used as marker material.

The orientation determination unit allows determining the location and orientation of the asymmetric marker and, thus, of the catheter to which the asymmetric marker is attached.

The path of the catheter in a plane parallel to the two-dimensional detection surface can be inferred from a sequence of asymmetric markers or from an additional linear marking element being preferentially a wire running along the centre of the catheter. The angulation orthogonal to the two-dimensional detection surface can be inferred due to the special shape of the asymmetric markers. The appearance of the ring element in the projection image determines the angle between the two-dimensional detection surface and the catheter: For a catheter running parallel to the two-dimensional detection surface, the ring element will be seen as a line only, for the catheter running orthogonal to the two-dimensional detection surface the ring will be seen as a circle. For all other angulations the ring element will appear as an ellipse, whose eccentricity determines the catheter angle with respect to the detector plane. The remaining ambiguity, if the catheter is inclined towards the two-dimensional detection surface or away from it, is resolved by analyzing the asymmetric elements.

As already mentioned above, in a preferred embodiment the asymmetric markers are attached to the catheter with different rotations around the catheter axis such that some asymmetric elements are always visible with little foreshortening regardless of the rotation of the catheter around its axis.

The orientation determination unit is adapted to detect the asymmetric markers in the projection image. This is easily possible by known image processing methods, because the shape of the asymmetric markers is exactly known.

The catheter path can be reconstructed in three-dimensions in real-time from a single X-ray projection, without using additional tracking systems. This simplifies navigation during the intervention and allows for registration with and navigation inside pre-operatively acquired three-dimensional images.

If the asymmetric element is v-shaped, wherein the two legs have a different length, the orientation of the asymmetric marker can easily be determined from the projection image due to the longer leg of the asymmetric element and the possible additional spherical element at its end.

The metal wires and/or the spherical end elements are preferentially made of gold.

Figure 7:
Figure 8:
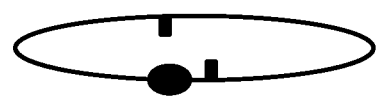
Figure 9:

Although in the above described embodiments, the asymmetric marker is a ring element comprising certain asymmetric elements, in another embodiment the asymmetric marker can be another marker being asymmetric under mirroring with respect to all spatial axes. Examples of asymmetric markers are shown in FIGS. 7 to 9. These asymmetric markers comprise a ring element and asymmetric elements attached to the ring element. It should be noted that the asymmetric elements are not mandatorily asymmetric, in particular, with respect to all spatial axes. The asymmetric elements are elements that render the asymmetric marker asymmetric, if the asymmetric elements are attached to the ring element.

Although in the above described embodiments the asymmetric marker comprises a ring element, wherein two or more asymmetric elements are attached to the ring element, in other embodiments, only a single asymmetric element can be attached to the ring element, wherein this single element is adapted such that the combination of the ring element and the asymmetric element forms an asymmetric marker being asymmetric under mirroring with respect to all spatial axes. Such an asymmetric marker having a ring element and an asymmetric element attached to the ring element is for example an asymmetric marker comprising a ring element and a single v-shaped asymmetric element having legs being distinguishable in the projection image like the v-shaped asymmetric element shown in FIGS. 2 and 3.

The term "an asymmetric marker attached to the catheter" includes that the asymmetric marker is a separate marker attached to the catheter and that the asymmetric marker is an integral part of the catheter.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for determining the orientation of a catheter, the system comprising:
    a catheter,
    an asymmetric marker attached to the catheter,
    an imaging unit configured to generate a projection image of the asymmetric marker, wherein the imaging unit comprises a radiation source for generating radiation for projecting the asymmetric marker in a projection plane and a detection unit configured to generate the projection image of the asymmetric marker projected in the projection plane, and
    an orientation determination unit configured to determine the orientation of the asymmetric marker from the projection image of the asymmetric marker and to determine the orientation of the catheter from the orientation of the asymmetric marker,
        wherein the asymmetric marker is configured such that the orientation of the asymmetric marker is determinable from the projection image of the asymmetric marker alone, wherein the asymmetric marker comprises a ring element configured to fit around the catheter and an asymmetric element comprising two legs having different lengths protruding outward from the ring element, and attached to the ring element forming a v-shape;
        wherein the two legs are configured to be distinguishable and separately identifiable from each other in the projection image.

2. The system as defined in claim 1, wherein the asymmetric marker is asymmetric under mirroring with respect to all spatial axes.

3. The system as defined in claim 1, wherein the asymmetric marker comprises at least one additional asymmetric element attached to the ring element.

4. The system as defined in claim 3, wherein the at least one additional asymmetric element is v-shaped, wherein two legs of the at least one v-shaped asymmetric element are configured to be distinguishable in the projection image.

5. The system as defined in claim 3, wherein the orientation determination unit is configured to determine the degree of angulation with respect to the projection plane from the eccentricity of the ring element in the projection image and to determine the direction of angulation with respect to the projection plane from the arrangement of at least one asymmetric element in the projection image.

6. The system as defined in claim 5, wherein
    the two asymmetric elements are v-shaped,
    the two legs of each v-shaped asymmetric element have different lengths and are distinguishable in the projection image,
    for both asymmetric elements a connection point of the two legs is attached to the ring element,
    the two asymmetric elements are arranged at opposite sides of the ring element with respect to a plane in which the ring element is located,
    if in a clockwise direction a first leg of one of the asymmetric elements is located in front of a second leg, in the counter-clockwise direction the first leg of the other of the asymmetric elements is located in front of the second leg, and
    the orientation determination unit is configured to determine that the catheter is tilted
        away from the projection plane, if a) the asymmetric elements appear inside the ring element and for both asymmetric elements the first leg appears left of the second leg or b) the asymmetric elements appear outside of the ring element and for both asymmetric elements the first leg appears right of the second leg, and
        towards the projection plane, if c) the asymmetric elements appear inside the ring element and for both asymmetric elements the first leg appears right of the second leg of the asymmetric elements or d) the asymmetric elements appear outside of the ring element and for both asymmetric elements the first leg of the asymmetric elements appears left of the second leg.

7. The system as defined in claim 1, wherein the system comprises a multitude of asymmetric markers, wherein the multitude of asymmetric markers are attached in predefined intervals along the catheter.

8. The system as defined in claim 7, wherein the multitude of asymmetric markers is attached to segments of the catheter, wherein the orientation determination unit is configured to determine the orientation of the multitude of asymmetric markers from the projection image and to determine the orientations of the segments of the catheter from the determined orientation of the multitude of asymmetric markers, wherein the orientation determination unit further comprises a catheter model providing unit configured to provide a model of the catheter and a catheter path determination unit configured to determine a path of the catheter by arranging the provided model of the catheter such that it corresponds to the determined orientations of the segments of the catheter.

9. A catheter comprising an asymmetric marker for determining the orientation of the catheter from a determined orientation of the asymmetric marker, wherein the asymmetric marker is configured to allow determining the orientation of the asymmetric marker from a projection image of the asymmetric marker alone generated by an imaging unit comprising a radiation source configured to generate radiation for projecting the asymmetric marker in a projection plane and a detection unit configured to generate the projection image of the asymmetric marker projected in the projection plane,
    wherein the asymmetric marker comprises a ring element configured to fit around the catheter and two legs having different lengths protruding outward from the ring element and attached to the ring element forming a v-shape, wherein the two legs are configured to be distinguishable and separately identifiable from each other in the projection image.

10. A method for determining the orientation of a catheter comprising an asymmetric marker, the method comprising following steps:
    providing the catheter and the asymmetric marker comprising a ring element configured to fit around the catheter and two legs having different lengths protruding outward from the ring element and attached to the ring element forming a v-shape,
    generating a projection image of the asymmetric marker by an imaging unit, wherein the imaging unit comprises a radiation source configured to generate radiation for projecting the asymmetric marker in a projection plane and a detection unit configured to generate the projection image of the asymmetric marker projected in the projection plane, wherein the two legs are configured to be distinguishable and separately identifiable from each other in the projection image,
    determining the orientation of the asymmetric marker from the projection image of the asymmetric marker alone, and
    determining the orientation of the catheter from the orientation of the asymmetric marker.

11. A non-transitory computer readable storage medium comprising a computer program for determining the orientation of a catheter comprising an asymmetric marker, wherein the computer readable program when executed on a computer causes the computer to perform the steps of claim 10.

12. An orientation determination method comprising following steps:
   providing a catheter and an asymmetric marker attached to the catheter, the asymmetric marker comprising a ring element configured to fit around the catheter and two legs having different lengths protruding outward from the ring element and attached to the ring element forming a v-shape,
   generating a projection image of the asymmetric marker by an imaging unit, wherein the imaging unit comprises a radiation source configured to generate radiation for projecting the asymmetric marker in a projection plane and a detection unit configured to generate the projection image of the asymmetric marker projected in the projection plane,
   determining an orientation of the asymmetric marker from the projection image of the asymmetric marker, wherein the two legs are configured to be distinguishable and separately identifiable from each other in the projection image,
   determining the orientation of the catheter from the orientation of the asymmetric marker,
   wherein the asymmetric marker is adapted such that the orientation of the asymmetric marker is determinable from the projection image of the asymmetric marker alone.

13. A non-transitory computer readable storage medium comprising a computer program for determining the orientation of a catheter comprising an asymmetric marker, wherein the computer readable program when executed on a computer causes the computer to perform the steps of claim 12.

* * * * *